United States Patent [19]

Peterson et al.

[11] 4,135,386

[45] Jan. 23, 1979

[54] POROUS MATERIAL CRACK DETECTION

[75] Inventors: Marvin L. Peterson; Donald H. Oertle, both of Ponca City, Okla.

[73] Assignee: Continental Oil Company, Ponca City, Okla.

[21] Appl. No.: 864,575

[22] Filed: Dec. 27, 1977

[51] Int. Cl.² ............................................ G01N 19/06
[52] U.S. Cl. .......................................... 73/40; 73/104; 340/605
[58] Field of Search .................... 73/40, 104; 340/605, 340/540

[56] References Cited

U.S. PATENT DOCUMENTS

| 2,516,857 | 8/1950 | De Forrest et al. | 73/104 |
| 2,635,329 | 4/1953 | De Forrest et al. | 73/104 |

*Primary Examiner*—S. Clement Swisher
*Attorney, Agent, or Firm*—Cortlan R. Schupbach, Jr.

[57] ABSTRACT

This invention provides a method for monitoring early formation of cracks in permeable or porous materials which comprises affixing a frangible fluid impermeable enclosure to the permeable or porous surface to be monitored such that a crack forming in the permeable material will destroy the integrity of the frangible fluid impermeable enclosure and provide a passage for a fluid to flow between the environment and the enclosed space, then sealing a fluid passageway in fluid communication from the enclosed space to a source of pressure different than ambient at the permeable material and to a pressure sensor; then imparting a pressure different than ambient to the enclosed space through the fluid passageway and thereafter monitoring the internal pressure in the enclosed space and fluid passageway with a pressure sensor such that a crack in the permeable material will destroy the integrity of the enclosed space and allow passage of fluid between the environment and the enclosed space which is detected by the pressure sensor.

27 Claims, 7 Drawing Figures

POROUS MATERIAL CRACK DETECTION

This invention relates to early detection of crack formation in porous or permeable non-structural members subject to stress. More specifically, this invention relates to a method for the early detection of crack formation in permeable materials through the use of frangible and closed spaces upon the surface to be monitored.

Crack formation in permeable or porous members subject to stress is a problem long recognized and one which has received much attention in recent years. For example, in an effort to conserve space and move larger amounts of natural gas, often such materials are liquified and placed in concrete containers which have cryogenic properties much superior to steel or metal containers. Such containers are being fabricated and located in more and more locations around the world. As a further illustration, many ships made of concrete have been made or designed to carry liquified natural gas (LNG) at very low cryogenic temperatures, the concrete cargo container being much superior to insulated steel at the temperatures encountered.

Various attempts have been made to detect cracks in such materials, the most common being visual inspection. When such visual inspection cannot be made, such as beneath the surface of water in tankers or below ground level in tanks, the common practice has been to place a material such as a dye in the contents of the container so that any cracks which penetrate the container will allow visual detection of the contents. This method is commonly known as the Dye-Check method. However, this method is not practical particularly in the case of flammable materials which are maintained at extremely low temperatures since a crack which penetrates completely through and releases the contents of such vessels can be catastrophic with regard life, material, and energy production.

Acoustic emission methods have also been employed but are not noticeably effective in non-permeable porous materials since these tend to dampen sound and give misleading results. In addition, these methods require relatively complex expensive equipment which detect cracks only while the cracks are forming.

The art recognizes that metallic materials can be checked using magnetic methods. However, this method is not practical for application to permeable or porous, and non-magnetic materials and in other applications.

Ultrasonic tests have also been employed in the prior art. These methods, however, are surface geometry dependent and require smooth surfaces without voids in order to give an accurate reading. It is clear that porous or permeable materials such as those covered by the instant invention would not be effectively protected or monitored by such methods.

Our co-pending application U.S. Ser. No. 778,660 teaches a method of detecting early crack formation by welding or attaching a solid metal plate over the area to be monitored applying a pressure differential and detecting early formation of cracks by the loss of pressure encountered. However, this method is likewise not possible on porous permeable materials.

U.S. Pat. No. 3,667,862 discloses a method for detecting a crack in the wall of a hollow object by reducing pressure on the inside of the hollow body and sensing loss of the vacuum formed. However, this method is not suitable for detection of cracks in permeable or porous members since vacuum will be lost in the interior of such objects. This method also fails to detect the crack until the crack has completely penetrated the hollow body which is monitored.

Exemplary of references showing detection of leaks and vessels by forming a sealed cavity over a possible leak sight such as a joint or the like and then reducing pressure in the cavity to detect a leak by loss of the vacuum thus formed by tracer gas placed within the vessel or by soap bubbles are shown in U.S. Pat. Nos. 3,949,596; 2,660,053; 1,371,484; 3,043,129; 3,524,342, and 4,002,055. However, such methods are not suitable for the solution of the problems outlined heretofore for a variety of reasons. Initially, these methods relate to detection of leaks and closed vessels, not to detection of formation of cracks in permeable or porous objects. These methods also relate to the detection of pre-existing leaks and not to detection of cracks formed from environmental and wear conditions during a monitoring period which may extend over months or years. The instant invention thus constitutes a substantial advance in the art by providing early crack detection in permeable or porous solid materials subject to stress. The detection is made at a sufficiently early stage that corrective action can be taken. In so doing, the instant invention solves most major problems associated with crack detection in permeable or porous materials whether used in the art of offshore oil production and energy transportation or storage or other interprises. In addition, the instant invention provides an excellent intruder or intrusion alarm system which is not dependent upon electrical connections.

It is therefore an object of the instant invention to provide a process for early detection of cracks in permeable materials subject to stress before the cracks traverse the material. It is a further object of the instant invention to provide an alarm system which is not dependent upon electricity for effectiveness. Other objects will be apparent to those skilled in this art as the description proceeds.

Thus the instant invention can be described as a method for monitoring early formation of cracks in permeable materials comprising;
 a. affixing a frangible fluid impermeable enclosure to the permeable surface to be monitored such that a crack forming in the permeable material will destroy the intregity of the frangible, fluid impermeable enclosure and provide a passage for a fluid to flow between the environment and the enclosed space;
 b. sealing a fluid passageway in fluid communication from the enclosed space to a source of pressure different than ambient at the permeable material and to a pressure sensor;
 c. imparting a pressure different than ambient to the enclosed space in the fluid passageway; and
 d. monitoring the internal pressure in the enclosed space and fluid passageway with the pressure sensor, such that a crack in the permeable material will destroy the integrity of the enclosed space and allow passage of fluid between the environment and the enclosed space, thus changing the pressure which is detected by the pressure sensor.

A BRIEF DESCRIPTION OF THE DRAWINGS

DETAILED DESCRIPTION OF THE DRAWINGS

Figure 1:
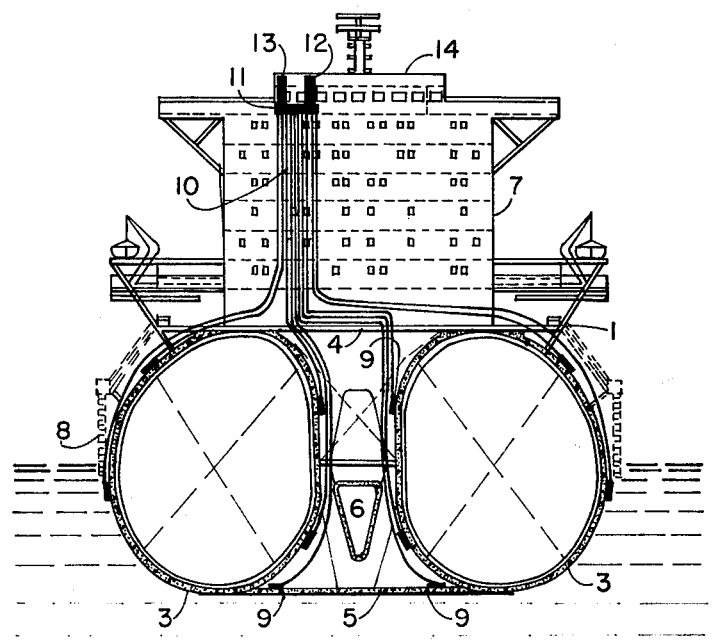
FIG. 1 is a cross-section of a concrete hulled tanker having an example of the apparatus of the instant invention aboard for monitoring the concrete hull portions.

FIG. 1 illustrates a cross-section of a ship having a concrete hull, the apparatus of this invention affixed thereto.

The ship decking (1) overlies and is affixed to concrete hull members (3) which are connected by upper concrete decking (4) and lower concrete decking (5). The ship is comprised of various other members well known to those skilled in this art such as boyancy and reserve fuel containers (6), bridge and superstructure (7) side plating (8) and so forth. The enclosed spaces (9) of the instant invention are connected by fluid passageways (10) to a central manifold and controller (11), and also include communication with a vacuum source (12). The enclosed spaces can be of any configuration desired but clearly to monitor areas of this size a serpentine or zig zag fashion would be most effective. The vacuum manifold and controller (11) is connected to a vacuum read out (13). The controller (11) and readout (13) combination has the ability to sequentially monitor the enclosed spaces and provide an alarm when leakage of any enclosed space is detected by the loss of the pressure differential in the line associated therewith. The manifold and controller will normally be sheltered in the bridge area (14) of the superstructure (7) for constant monitoring and quickness of response.

Figure 2:
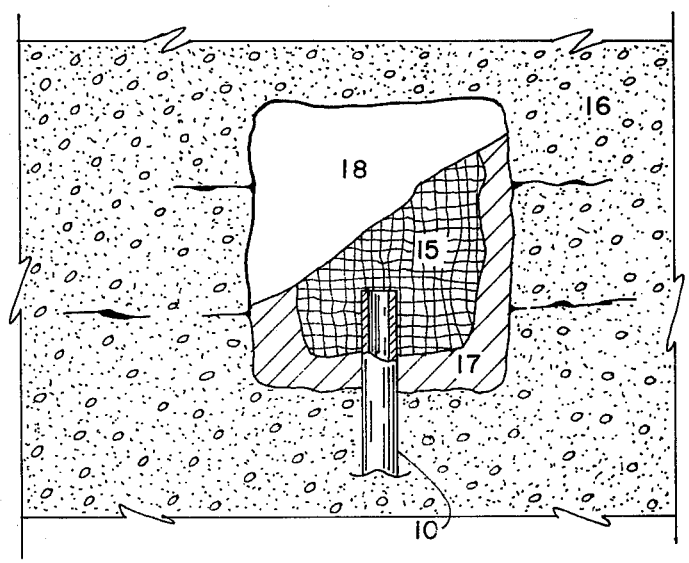
FIG. 2 illustrates a top sectional view of an enclosed space attached to a concrete member.

FIG. 2 illustrates a top sectional view of a fluid tight enclosed space. Fluid passageway (10) is in fluid communication with a fluid permeable material (15) which is affixed to the concrete (16) member to be monitored by a frangible, fluid impermeable adhesive (17). The entire enclosed space is rendered both enclosed and fluid tight by a thin layer of a frangible and permeable material (18) such as a metal foil.

Figure 3:
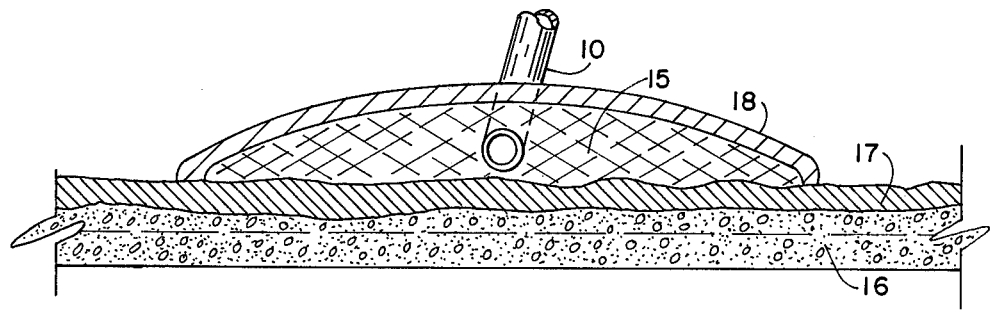
FIG. 3 illustrates a cross-sectional view of an enclosed space wherein the enclosed space comprises a sealant overlying a permeable material, overlying a frangible fluid impervious adhesive which is affixed to the concrete.

FIG. 3 illustrates by cross-sectional view the enclosed space set forth in FIG. 2 wherein the fluid passageway (10) is in fluid communication with a fluid permeable material (15) which overlies a frangible fluid impermeable adhesive (17) affixing the entire enclosed space to the area to be monitored (16).

Figure 4:
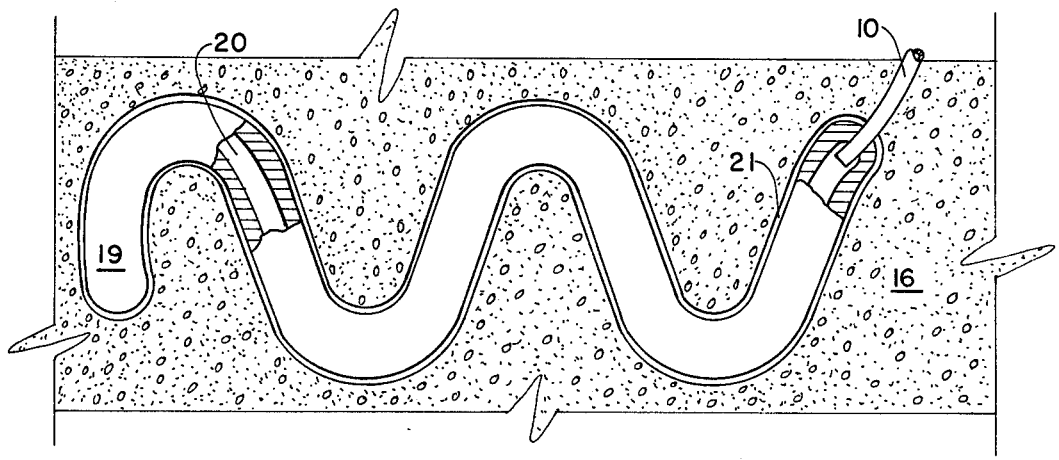
FIG. 4 illustrates an enclosed area made of glass having a serpentine configuration which monitors a large area of the material to be protected.

FIG. 4 illustrates an embodiment of the instant invention wherein the enclosed space is a glass tube (19) affixed to the material to be protected (16). The glass tube is frangible and is sealed to a fluid passageway (10) at one end. It should be noted that the interior (20) of the glass tube contains no material. The entire enclosed space is affixed to the material to be monitored (16) by an adhesive (21). In this embodiment, wherein the adhesive is entirely outside the enclosed space and does not form one portion thereof, the adhesive need not be either impermeable or frangible, but merely sufficient to firmly adhere the entire enclosed space to the surface to be monitored, such that a crack propagating along the surface of the material to be monitored will rupture the integrity of the enclosed space and allow fluid communication with the ambient environment.

FIG. 8 illustrates another embodiment of the instant invention shown in a serpentine fashion. In this invention the enclosed space is formed of a thin metal foil (22) which is supported over a fluid permeable material (23) such as a cloth or wire wick, said foil sealed in fluid tight communication with a fluid passageway (10). Again the adhesive need not be either impermeable or frangible but merely affix the enclosed space firmly to the object to be monitored.

Figure 6:
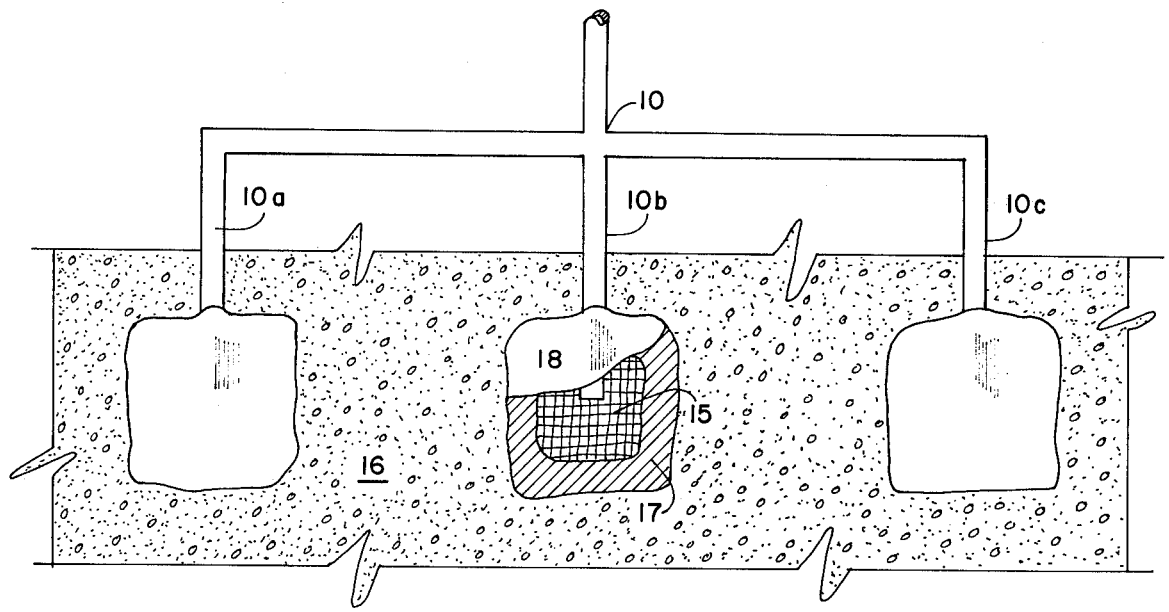
FIG. 6 illustrates an embodiment of the instant invention wherein a series of enclosed spaces are employed to monitor separate areas of the material wherein a common line is used.

FIG. 6 illustrates by top sectional view an embodiment of the instant invention wherein a plurality of patches are employed to monitor various portions of the surface (16). Again the fluid passageway (10) is common to all enclosed spaces such that a loss of pressure differential from ambient anywhere in the system can be easily detected. Enclosed spaces depicted are those using a frangible, fluid impermeable sealant (17) to which is adhered fluid permeable material (15), all made fluid impermeable by a fluid impermeable layer (18). However, it is clearly understood that other types of enclosed spaces such as glass tubes or metal foils supported on fluid permeable wire rope or fiber rope can be employed in their place. All enclosed spaces are joined through the manifold (10) and the fluid passageways (10a, 10b, and 10c).

Figure 7:
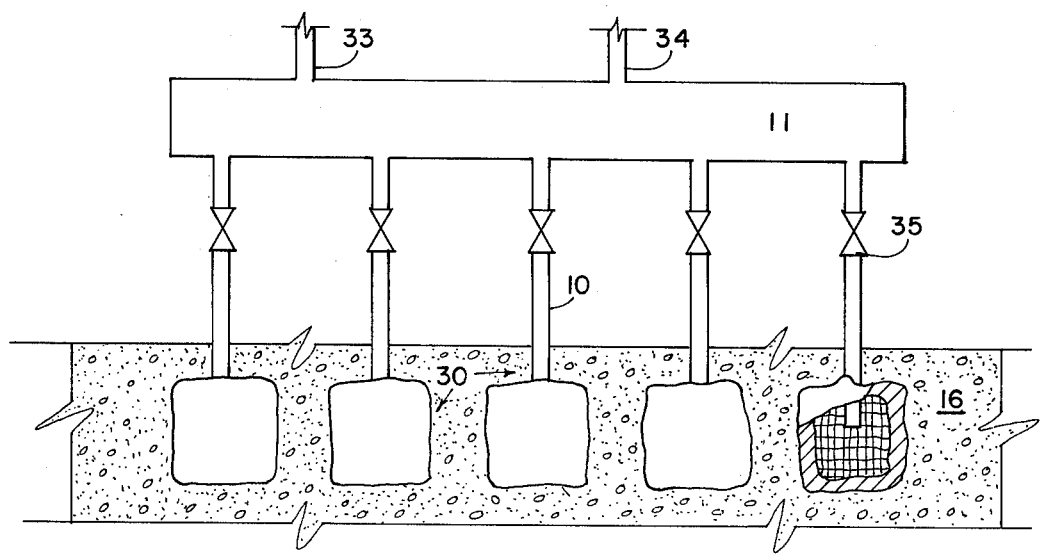
FIG. 7, in contrast, is a schematic illustration of an embodiment wherein a series of enclosed spaces are monitored using separate lines and a system whereby the failure area can be isolated.

FIG. 7 schematically illustrates yet another embodiment of the instant invention wherein enclosed spaces (30) over the material to be monitored (16) are joined by lines (10) to the manifold (11). Line 34 connects to a vacuum source while line 33 leads to the readout and pressure monitoring. Valves 35 are sequentially switched and the pressure in each of the lines is monitored to specifically locate on a readout (usually with an alarm) which of the enclosed spaces is indicating loss of pressure differential, and consequently the probability of crack formation.

According to the instant invention, the enclosed spaces provided are placed on the surface to be monitored such that a crack forming in the surface will rupture the frangible enclosed space and allow fluid communication between the environment and the cavity without passing through the entire member. It is apparent that a fluid passageway can be connected to a pressure source either higher or lower than ambient, but of these lower than ambient is preferred for several reasons.

Initially, a lower than ambient pressure source is a more efficient method of detecting pressure differentials since nature fills a vacuum and any rupture of the sealed enclosure will rapidly be filled by the outside environment. In contrast, a higher than ambient pressure source can, under some circumstances, be difficult to monitor. For example, referring again to FIG. 1, it can be seen that a portion of the detectors in the ship holes are under the surface of the water and are thus subject to different pressures from the outside environment than those above the water line. In this situation a lower than ambient (vacuum) source would be preferred since source differentials would not be necessary in order to provide the same amount of protection. For example, if higher than ambient pressure were used on a ship hull, the sensors located beneath the hull furthest from the water line would require a higher pressure to give the same reading as those above the water line. In contrast, the vacuum would merely draw the ambient environment into the formerly sealed space, indicating a pressure differential and an alarm would be sounded.

Thus in the preferred embodiment the pressure imparted to the cavity is very low pressure or a vacuum. The vacuum employed can be in the millitor range for most applications, since devices to measure these low pressures are very sensitive, reliable, and relatively inexpensive.

In addition to merely detecting cracks, the apparatus of the instant invention is extremely suitable for alarm systems for many purposes. For example, an intruder alarm using the enclosed space fluid passageway and sensors of the instant invention would be failsafe as compared to existing systems. Such enclosed spaces could be placed upon the walls of buildings, doorways, windows, etc. such that breakage or fracturing thereof would allow fluid communication with the ambient environment and an alarm could be triggered. In a preferred embodiment for an intruder alarm system, the alarm would be a pressure powered alarm, thus completely eliminating the need for electrical maintenance and eliminating the possibility of electrical bypass, since no way is known that the vacuum can be maintained once the sensors are ruptured to the environment.

An alternative embodiment of the intruder alarm system would be a material such as that described in FIG. 2 or FIG. 3, wherein the covering material (18) is temperature sensitive, such that a fire or flame in the vicinity of the enclosed space will rupture or melt the frangible surface and allow ambient pressure into the closed system. Thus the method would make a very suitable fire or heat detector which is inexpensive and which monitors continuously.

Yet another embodiment of the instant invention would be to make the enclosed material (18) or the frangible adhesive (17) sensitive not only to heat but solvents and/or water to detect flooding or solvent release. Such systems are reliable and inexpensive and solve much of the problems currently filled by much more expensive untested equipment. These systems would find application in mines, tunnel passing under or through bodies of water and other applications where continuous monitoring would be beneficial. Detection of cracks in support members and roof and well portions of mines in yet another application of such alarm systems.

It will, or course, be realized that when used as an alarm, whether for intruders, fire, water, or solvents, these enclosed sealed spaces need not be affixed to permeable or porous materials alone but can indeed be affixed to any surface such as glass, wood, paper, plastic, cooler rack, which is in the area to be monitored. For example, an intruder alarm could be easily fixed across glass windows, fire alarms could be attached to wooden surfaces in areas where flammable liquids are stored or flames are likely to occur, and solvent sensitive enclosed spaces could be placed in conduits or passageways where solvents would be expected if released from normal confinement. Representative examples of such materials would be in ships to detect leaks, either from solvents being carried or from water entering spaces above normal level, and ships and elsewhere for paint stores and other flammable material, and in concrete wooden or other porous permeable materials in which early crack detection is required. The system would be beneficial for monitoring underground radioactive waste burial in a reliable manner for long lengths of time.

It will be apparent that a plurality of fluid and permeable enclosed spaces can be affixed to surfaces to be monitored. In preferred embodiments the fluid passageway is a metal or plastic tube and the frangible enclosure would be affixed to the permeable or porous material with an epoxy base sealant. Preferably, the pressure imparted to the cavity is a negative or very low pressure (vacuum) and the plurality of sensors are designed to activate a common alarm system. Further preferred is where the plurality of sensors activate a common alarm system which indicates which of the sensors have been activated. It will be readily apparent that the instant invention can be likewise be applied to a plurality of articles rather than a plurality of sensors upon one article or in the alternative that multiple sensors can be used upon multiple articles.

Frangible materials such as glass tubes or metal foils surrounding the fluid permeable material such as a wire or fiber cloth or wire or fiber rope or fluid porous paper can be used to prop a thin metal foil which when sealed to the surface to be monitored will easily rupture and provide notice of failure to the sensors.

The metal foil over a fluid permeable substrate (called a propped foil) can be adhered directly to the surface to be monitored.

Alternatively, an impermeable frangible adhesive can be affixed to the permeable surface and a fluid impermeable material placed on the adhesive to form a fluid tight enclosed space on the impermeable frangible adhesive such that a crack propagating through the permeable material will destroy the integrity of the enclosed space through the frangible adhesive and allow fluid communication to the environment. Alternatively, the enclosed space can be formed by simply applying an additional coat of the fluid impermeable frangible adhesive over a fluid permeable material into which the fluid passageway is inserted thus providing a frangible enclosed space.

Figure 5:
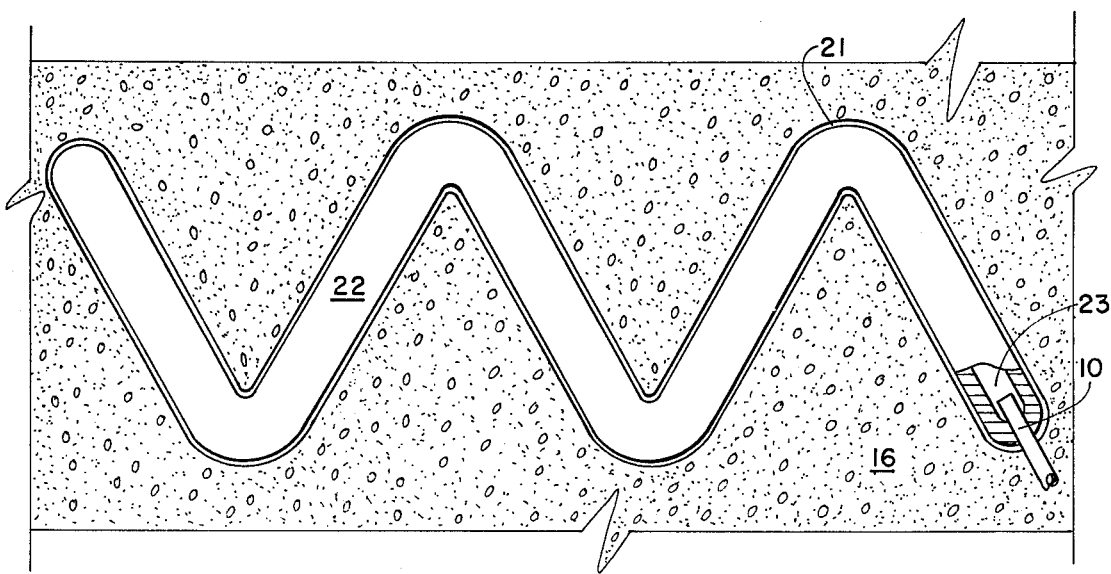
FIG. 5 illustrates a zig zag configuration much as FIG. 4 illustrates a serpentine configuration.

As set forth in FIGS. 4 and 5 the enclosed spaces can be elongated and placed to cover substantial portions of the permeable material, thus providing a much wider monitoring range.

In addition, there is provided a failsafe non-electric alarm apparatus comprising a fluid pressure source and fluid communication through a fluid passageway with a sensor unit and a pressure detector designed to activate an alarm upon a change of pressure in the system. This apparatus can then be connected to a detector, preferably one with a diaphragm holding a spring loaded valve closed wherein the loss of vacuum allows the opening of the valve to sound a pressure powered alarm. The apparatus can be adapted to provide either intrusion alarms, fire alarms, water alarms, or solvent alarms designed to indicate leaks of hazardous material.

The fluid passageways from the sensors can be shunted by suitable valve arrangements to differential pressure transducers such as described in U.S. Pat. No.

3,505,634 or a thermocouple gauge. Thereafter, vacuum lost in the line between the transducer and the enclosed space due to destruction of the integrity of the enclosed space allows the transducer to provide a signal indicating the pressure difference. This can be electrically connected to trigger an alarm such as a light, bell or the like or more preferably to open a pressure powered switch which will activate a pressure powered alarm thus eliminating the need for electricity and obviating system failure with electrical failure.

While a sensor and ion pump can be provided for each closed space, alternatively one or more differential pressure transducers can be employed with sequential scanning of the various lines between the enclosed spaces and the pressure source through the transducer.

According to another preferred embodiment, the vacuum line from each enclosed space connects to a vacuum manifold which is evacuated with a conventional mechanical pump employing cold traps, absorbants and the like. High vacuum can be obtained with an ion pump. A thermocouple gauge can be positioned in each line between the enclosed space and the manifold. Upon penetration of the enclosed space by whatever means, fluid enters and the differential pressure is detected by the thermocouple gauge which triggers an alarm and activates a solonoid actuated valve situated in the vacuum line between the thermocouple gauge and the vacuum manifold. Advantages of this arrangement are that each individual enclosed spaced line is monitored and high vacuum is not lost in the system upon a single enclosed space losing vacuum. The time and trouble needed to isolate the open line and rebuild vacuum, first with a conventional pump and then with the ion pump, is thus avoided. In addition, the system is not contaminated with fluid leaking in and monitoring is continued without a breakdown due to the entire system coming to ambient pressure. An alternative or backup system using a pressure powered alarm could be, of course, inserted in conjunction with an electrical system. This embodiment is of particular value when a large number of sites on structures such as offshore platforms and ships are monitored.

The vacuum or high pressure source employed can be any conventional device for producing vacuum or pressure. Thus a conventional vacuum pump can be employed to reduce pressure to a low level. Suitable absorbants, cold traps, and the like can be employed. High vacuum can readily be provided with suitable ion pumps which are readily available.

In a preferred embodiment for use upon an offshore platform or ship the pumping system is fabricated to handle up to 100 detectors and to produce a pressure of about $10^{-5}$ torrs for the first day with steadily declining pressure for several days to about $10^{-7}$ torr. The vacuum system, of course, can be designed for the particular monitoring system employed and this is well within the skill of engineers in this art or can be readily determined by simple experimentation. The vacuum and monitoring system can be fabricated largely of conventional off-the-shelf hardware, considerable varieties of which are available, for example, from the Varian Company.

The sealant employed according to this invention can be any of a number of sealants. For example, solder, brazing material, epoxy base sealants, silicone material Woods metal, butyl rubber sealants, hot melt formulations, and any variety of other materials can be employed if desired and for the purpose desired.

According to the present invention, a very suitable and versatile material which has been found to be satisfactory is KNEADATITE sealant, Trademark of and sold by Polymeric Inc, Pottstown, PA. This material is a epoxy/polyamide system which is supplied as a two-part hand mixable tape which is kneaded together and cures within a few hours. This epoxy base sealant is easily formed into the covering for an enclosed space within one hour after mixing and cures into a flexible, tough, hard well-adhering material. It can be applied under water and has been found to make quite suitable bonds in its use as a sealant described according to this invention. Representative examples of frangible adhesives which would fit under the sealant described above is epoxy adhesive and rigid thermoplastic adhesives. The strength of most adhesives is limited to about 3,000 pounds per square inch which is the strength level for low quality concrete. It would be important to select an adhesive with a strength equal to or less than the permeable material being tested.

The permeable material described above which is encased within the enclosed spaces of the instant invention can be any material which will hold the cavity open to the flow of fluid when vacuum is supplied. Suitable materials include paper, cloth prepared of natural or synthetic fibers, open cell foam plastics, and the like. A fabric woven of synthetic fibers is quite suitable. Alternatively, however, the patch can have a wire member or the like extending from the end of the fluid line which props up a foil sheet or similar cover to hold open a vacuum passage under the sealant of the enclosed space.

The fluid impermeable material over the fluid permeable material can be any of a number of substances which are impermeable to fluids. For example, thin metal foil such as aluminum foil, polyester terephthalate plastic films (such as trademarked Milar film) are quite suitable. The porous material or bleeder material is overlain with this impermeable barrier such as described in the drawings in FIG. 3.

Adhesive suitable for affixing the enclosed spaces to the porous surfaces or in the case of the alarms to other surfaces can be any suitable adhesive which will securely fasten to both the impermeable barrier and the surface to be protected. Examples include commercially available epoxy resins, silicone base adhesives, cyanoacrylate based adhesives and the like.

Though the invention has been primarily described in terms of vacuum, that is very low pressure, and vacuum has been described as a preferred embodiment, it should be understood that pressure above ambient at the enclosed space can also be employed. Any suitable fluid, preferably air or an inert gas, can be employed for this positive pressure embodiment. However, if positive rather than negative pressure is employed, care must be taken not to exceed the pressure containable by the sealants in the enclosed spaces and lines employed.

While certain embodiments and details have been shown for the purpose of illustrating this invention, it will be apparent to those skilled in this art that various changes and modifications may be made herein without departing from the spirit or the scope of the invention.

We claim:

1. A method for monitoring early formation of cracks in permeable materials comprising (a) affixing a frangible, fluid impermeable enclosure to the permeable surface to be monitored such that a crack forming in the permeable material will destroy the integrity of the frangible, fluid impermeable enclosure and provide a passage for a fluid to flow between the environment and the enclosed space, (b) sealing a fluid passageway in fluid communication from the enclosure to a source of pressure different than ambient at the permeable material and to a pressure sensor, (c) imparting pressure different than ambient to the enclosure in the fluid passageway, and (d) monitoring the internal pressure in the enclosure and fluid passageway with the pressure sensor, such that a crack in the permeable material will destroy the integrity of the enclosure and allow passage of fluid between the environment and the enclosure and wherein the pressure change is detected by the pressure sensor.

2. A method as described in claim 1 wherein a plurality of fluid impermeable enclosures are affixed to the permeable material.

3. A method as described in claim 2 wherein the passageway is a metal tube and the frangible enclosure is affixed to the permeable material with an epoxy based seal.

4. A method as described in claim 3 wherein the pressure sensor activates an alarm system upon change of pressure in the system.

5. A method as described in claim 4 wherein a plurality of sensors activate a common alarm system.

6. A method as described in claim 5 wherein a plurality of sensors activate a common alarm system which indicates which of the sensors has been activated.

7. A method as described in claim 6 wherein a plurality of articles containing permeable materials are monitored.

8. A method as described in claim 7 wherein the articles are located on an offshore platform.

9. A method as described in claim 1 wherein an impermeable, frangible adhesive is affixed to the permeable surface and a fluid impermeable material is placed on the adhesive to form a fluid tight enclosed space on the impermeable frangible adhesive, such that a crack propagating through the permeable material will destroy the integrity of the enclosure through the frangible adhesive and allow fluid communication to the environment.

10. An apparatus for monitoring early formation of cracks in permeable materials comprising (a) a frangible fluid impermeable enclosure, (b) a fluid passageway sealed to and passing from the frangible enclosure to a source of pressure different than ambient and to a sensor providing fluid tight communication therebetween.

11. A method as described in claim 10 wherein the frangible fluid and impermeable enclosure is formed by an impermeable, frangible adhesive affixed to the permeable material and an impermeable material affixed to the frangible adhesive, forming an enclosure thereby, said enclosure being normally impermeable to fluid and providing a fluid tight seal to the outside environment.

12. A method as described in claim 11 wherein the impermeable material affixed to the adhesive is frangible.

13. An apparatus as described in claim 12 wherein the fluid tight passageway is a vacuum passageway, one end of the vacuum passageway is overlain by a permeable material, the permeable material is overlain by an impermeable barrier, and both are sealed from the environment by an impermeable seal.

14. The apparatus of claim 13 wherein sensors are elongated and placed to cover substantial portions of the permeable material and providing a wide monitoring range.

15. An apparatus as described in claim 14 wherein the sensor is designed to activate an alarm upon loss of vacuum in the system.

16. The apparatus of claim 3 wherein the frangible enclosures comprise glass tubing.

17. An apparatus as described in claim 15 wherein the sensor comprises a layer of frangible, impervious adhesive; overlying the adhesive, the end of the vacuum line; overlying the end of the vacuum line, a layer of a pressure-resistant fluid porous material; overlying the porous material, a layer of metallic foil covering the end of the vacuum line and the porous material; and overlying the entire foregoing, a layer of epoxy base sealant forming a fluid-tight barrier adhering the foil, the end of the vacuum line, and the frangible adhesive to the permeable material.

18. An apparatus as described in claim 17 wherein the fluid permeable material is wire or fiber cloth or wire or fiber woven rope.

19. An apparatus as described in claim 17 wherein the fluid porous material is a porous paper.

20. A fail-safe non-electric alarm apparatus comprising a fluid pressure source in fluid communication through a fluid passageway with a sensor unit and a pressure detector designed to activate an alarm upon a change of pressure in the system.

21. An apparatus as described in claim 20 wherein the sensor comprises a frangible, fluid impermeable enclosure situated such that the breakage or movement of a sensor will cause fluid passage into or out of the system.

22. An apparatus as described in claim 21 wherein the fluid pressure source is a vacuum source.

23. An apparatus as described in claim 22 wherein the detector is a diaphram holding a spring loaded valve closed, wherein the loss of vacuum allows opening of the valve to sound a pressure powered alarm.

24. An apparatus as described in claim 23 wherein the sensors are enclosures formed by foil supported by fluid permeable materials.

25. An apparatus as described in claim 24 wherein the enclosure comprises a frangible metal foil surrounding a permeable woven rope, said rope surrounding the end of a fluid passageway, the entire frangible apparatus sealed with a frangible sealant.

26. An apparatus as described in claim 24 wherein the sealant is selected to melt at a predetermined temperature and give alarm when said temperature is exceeded by allowing fluid flow into said enclosure.

27. An apparatus as described in claim 24 wherein the sealant is soluble or reactive, is employed to form a sensor which detects a solvent such as water or a reactant by allowing fluid flow into said enclosure.

* * * * *